United States Patent [19]

Murakami et al.

[11] Patent Number: 5,039,800

[45] Date of Patent: Aug. 13, 1991

[54] PROCESS FOR PRODUCING TRICHLOROISOCYANURIC ACID

[75] Inventors: Takashi Murakami, Chiyoda; Takami Ono; Yuzi Nishida, both of Nei, all of Japan

[73] Assignee: Nissan Chemical Industries, Ltd., Tokyo, Japan

[21] Appl. No.: 553,623

[22] Filed: Jul. 18, 1990

[30] Foreign Application Priority Data

Jul. 8, 1989 [JP] Japan .................................. 1-185754

[51] Int. Cl.$^5$ ............................................ C07D 251/36
[52] U.S. Cl. ............................................................ 544/190
[58] Field of Search ............................................ 544/190

[56] References Cited

U.S. PATENT DOCUMENTS 3,534,033 10/1970 Kagawa et al. ....................... 544/190
4,542,218 9/1985 Spooner ................................ 544/190
4,645,835 2/1987 Pieper .................................. 544/190

*Primary Examiner*—John M. Ford
*Attorney, Agent, or Firm*—Oliff & Berridge

[57] ABSTRACT

When trichloroisocyanuric acid is produced by a process which comprises supplying unreacted chlorine from a second reaction zone to a cooled mixture of cyanuric acid and an aqueous alkali solution in a first reaction zone to form a partially chlorinated alkali salt of cyanuric acid, and introducing the reaction product of the first reaction zone and chlorine into the second reaction zone to complete the chlorination of the reaction product from the first reaction zone, the supply of the chlorine into the second reaction zone is so controlled as to ensure that the mixture in the first reaction zone be maintained at a temperature of 5° C. to 20° C. The second reaction zone is advantageously defined by a vertically disposed loop-shaped reactor.

4 Claims, 2 Drawing Sheets

PROCESS FOR PRODUCING TRICHLOROISOCYANURIC ACID

BACKGROUND OF THE INVENTION

1. Field of the Invention

This invention relates to a process for producing trichloroisocyanuric acid known as having a particularly high effective chlorine content among the chlorinated isocyanuric acids which are hydrolyzable in water to release active chlorine and are, therefore, used as disinfectants and bleaches. More particularly, it is an improvement in the process which produces trichloroisocyanuric acid by two stages of reaction between a mixture of cyanuric acid and an aqueous alkali solution and chlorine.

2. Description of the Prior Art

The production trichloroisocyanuric acid by two stages of reaction between a mixture of cyanuric acid and an aqueous alkali solution and chlorine is disclosed in Japanese Patent Publication No. 24902/1965, U.S. Pat. No. 3,534,033, the Japanese patent application laid open under No. 4484/1973, etc. Japanese Patent Publication No. 24902/1965 teaches that it is possible to achieve a high yield of trichloroisocyanuric acid continuously if the redox potential of the reaction product in a second reaction zone is measured by a platinum/NKCl/calomel electrode and maintained in the range of 1050 to 1150 mV, and if the supply of the reactants is controlled in accordance with the redox potential.

U.S. Pat. No. 3,534,033 and the Japanese patent application laid open under No. 4484/1973 teach that it is possible to produce trichloroisocyanuric acid efficiently if an alkali salt of cyanuric acid is reacted with chlorine in a first reaction zone to form a reaction product having a pH of at least 9 (U.S. Patent) or at least 12 (Japanese application), and if chlorine is added to the reaction product of the first reaction zone in a second reaction zone to reduce the formation of nitrogen trichloride so that the reaction product may have a pH of 1.5 to 4. In other words, they rely upon the pH of the reaction product for the control of the reaction in each of the first and second reaction zones.

Referring to the process as taught by Japanese Patent Publication No. 24902/1965, however, it is necessary to measure the redox potential of the reaction product in the second reaction zone in which the crystals of trichloroisocyanuric acid are formed. The adherence of crystals to the electrode and the failure of the electrode, which is usually a glass electrode, to remain stable for a long time make it difficult to maintain a really sharp, accurate and reliable redox potential for a long period of time. A similar problem is likely to arise from the process which relies upon the pH of the reaction product as taught by U.S. Pat. No. 3,534,033, etc.

The formation of nitrogen trichloride as a highly explosive by-product is a matter which is not ignorable when trichloroisocyanuric acid is produced on an industrial basis. It is known that the formation of nitrogen trichloride can be kept to a minimum if the reaction product of the first reaction zone is reacted with chlorine gas quickly under stirring in the second reaction zone in which its chlorination is completed. When the reactor is of the tank type, however, it is necessary to use a larger stirrer to ensure the circulation of the reaction product from the first reaction zone and promote the dissolution of chlorine gas on which the rate of the reaction depends. Nevertheless, there is no assurance whatsoever that the formation of nitrogen trichloride can be completely prevented, but there is every likelihood that nitrogen trichloride may be formed and cause an abnormal reaction. Therefore, the chlorinating step of the process for producing trichloroisocyanuric acid calls for an expensive apparatus which is not only made of a chlorine-resisting material, but can also withstand a certain level of pressure.

SUMMARY OF THE INVENTION

We, the inventors of this invention, have done a great deal of work in search for a solution to the problems as hereinabove pointed out, and found that when trichloroisocyanuric acid is produced by two stages of reaction between a mixture of cyanuric acid and an aqueous alkali solution and chlorine, it is possible to achieve a high level of production efficiency continuously only if the supply of chlorine to the second reaction zone is controlled in accordance with the temperature of the first reaction zone.

We have also found that a vertical loop-shaped reactor which is known as being useful for the continuous reaction of gas and liquid can advantageously be used in the second reaction zone, since it does not require any large stirrer as is required for a reactor of the tank type, as the chlorine gas supplied into the reactor provides a driving force for circulating the reaction product from the first reaction zone, and since it can be constructed with a smaller diameter and a smaller wall thickness and is, therefore, less expensive than any reactor of the tank type.

It is, therefore, an object of this invention to provide a process which can produce trichloroisocyanuric acid efficiently and with a high level of operating stability over a long period of time.

This invention is an improvement in the process for the production of trichloroisocyanuric acid which comprises introducing unreacted chlorine from a second reaction zone into a cooled mixture of cyanuric acid and an aqueous alkali solution in a first reaction zone to effect partial chlorination of an alkali salt of cyanuric acid, and introducing chlorine and the reaction product of the first reaction zone into the second reaction zone to complete its chlorination.

According to a first aspect of this invention, the supply of chlorine into the second reaction zone is so controlled as to maintain the reaction product from the first reaction zone at a temperature of 5° C. to 20° C.

According to a second aspect of this invention, a vertical loop-shaped reactor is used in the second reaction zone, chlorine and the reaction product of the first reaction zone are introduced into the reactor near the lower end of an upstanding tubular portion thereof, unreacted chlorine gas is removed from the reactor at its upper end and is introduced into the first reaction zone, and the resulting slurry of trichloroisocyanuric acid is discharged from the reactor at its lower end.

Other features and advantages of this invention will be apparent from the following description and the accompanying drawings.

DETAILED DESCRIPTION OF THE INVENTION

Figure 1:
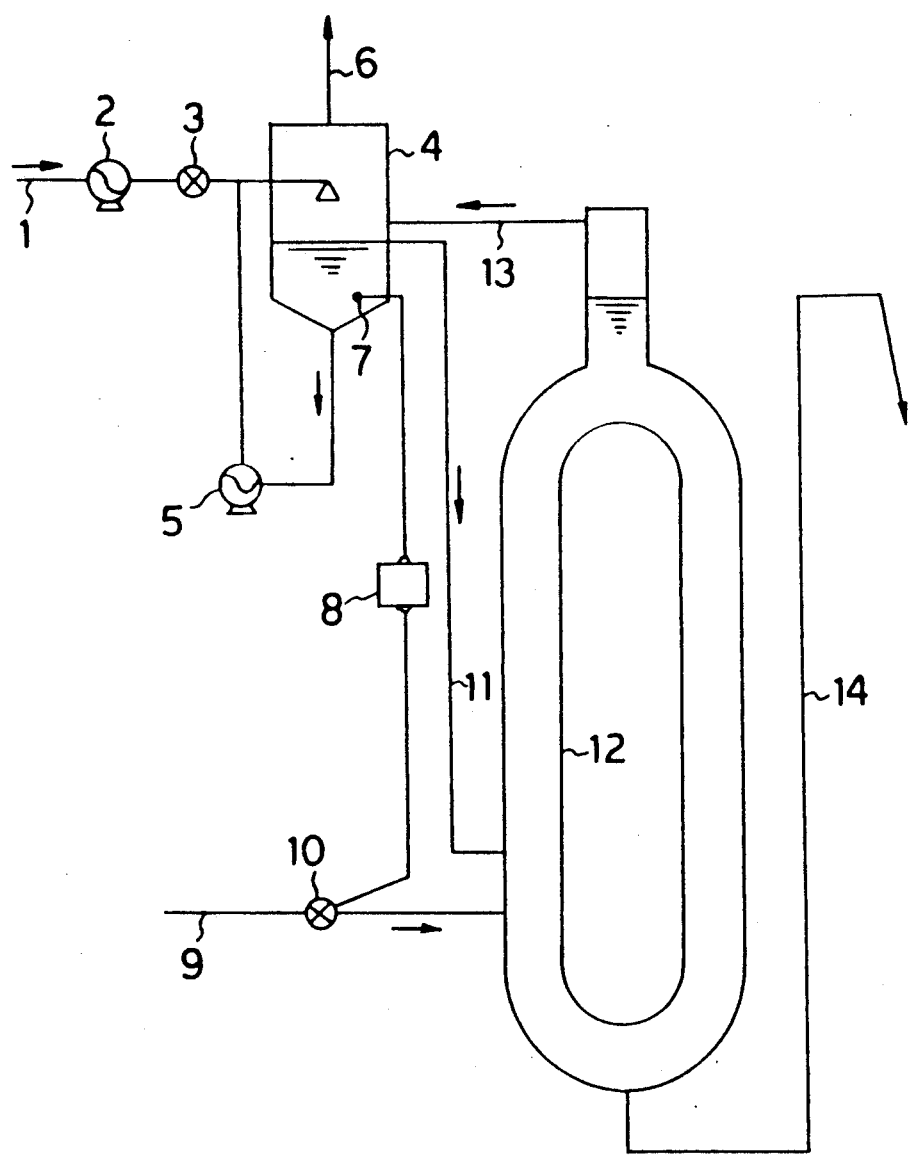
FIG. 1 is a block diagram of a reaction system employed for carrying out the process of this invention and including a loop-shaped reactor.

An alkali salt of cyanuric acid which is used as a feedstock is prepared as a mixture of cyanuric acid and an alkali hydroxide having a molar ratio of 1:3, and a cyanuric acid content of 20 to 60 g per liter. The mixture is cooled to a temperature between above its solidifying point and 10° C., and preferably not exceeding 5° C., before it is supplied into a first reaction zone. The cooled mixture of cyanuric acid and an aqueous alkali solution is introduced into the first reaction zone through a flow control valve, and contacted with reacted chlorine gas from a second reaction zone to undergo partial chlorination, as will later be described in further detail.

The control of the reaction in the first reaction zone is based on the temperature of the reactant mixture in the first reaction zone which is in turn so controlled by the unreacted chlorine from the second reaction zone as to remain within the range of 5° C. to 20° C. In other words, the supply of chlorine into the second reaction zone is so controlled as to ensure that the temperature of the reactant mixture in the first reaction zone remain within the range of 5° C. to 20° C. Therefore, no direct control is made of the reaction in the second reaction zone. The rate of the reaction for the formation of trichloroisocyanuric acid depends on the dissolution of chlorine gas and the subsequent chlorinating reaction is brought to an end instantaneously. Therefore, the control of supply of unreacted chlorine from the second reaction zone is sufficient for the control of the whole chlorinating reaction. The amount of the reactant mixture remaining in the first reaction zone is preferably between a half and one-tenth of that which remains in the second reaction zone, so that the temperature of the mixture in the first reaction zone may be sensitive to an increase or decrease in the supply of unreacted chlorine from the second reaction zone. The process which relies upon the temperature of the first reaction zone for reaction control as hereinabove described makes it possible to determine the state of the reaction quickly and accurately over a long period of time. This is due to, among others, the two reasons which will hereinafter be set forth:

(1) The instrument which is used for measuring the temperature for the reaction control remains reliable for a long period of time, as compared with any electrode used for determining the redox potential, or pH meter; and (2) No crystal is likely to adhere to the temperature measuring instrument, since the temperature is measured in the first reaction zone in which no crystallization occurs, or in which only a slurry having a very low concentration is formed, even if any crystallization may occur, as opposed to the determination of redox potential, or pH which is effected in the second reaction zone when the conventional process is employed.

The supply of chlorine into the second reaction zone is so controlled as to ensure that the reactant mixture in the first reaction zone remain at a temperature of 5° C. to 20° C., and preferably at a temperature of 8° C. to 15° C. The mixture is preferably maintained at a constant temperature within the range of 5° C. to 20° C. Any deviation from the constant temperature is so controlled as to fall within plus or minus 5° C., and preferably within plus or minus 2° C. If the temperature is lower than 5° C., the reaction is not completed in the second reaction zone, but some unreacted matter is left behind. If the temperature exceeds 20° C., crystallization undersirably occurs in the first reaction zone. Any temperature variation beyond plus or minus 5° C. must be avoided, as it brings about a great variation in the supply of chlorine to the second reaction zone and thereby a low yield of trichloroisocyanuric acid.

Although there is no particular limitation to the reactors which are used for carrying out the process of this invention, it is preferable to use a vertical loop-shaped reactor as far as the second reaction zone is concerned.

According to the second aspect of this invention, a vertical loop-shaped reactor is used for the second reaction zone. It comprises two upstanding parallel tubular portions connected together at the upper and lower ends thereof. One of them serves as an uptake, and the other as a downtake. A partially chlorinated alkali salt of cyanuric acid from the first reaction zone and chlorine are introduced into the uptake near its lower end. It is mainly a liquid containing crystals of trichloroisocyanuric acid that is conducted through the downtake, while the greater part of unreacted chlorine gas is drawn out of the reactor at its top into the first reaction zone, and the resulting slurry of trichloroisocyanuric acid is discharged from the reactor at its bottom. The gas-liquid mixture in the uptake has a greater proportion of gas than that in the downtake, and the resulting difference in density therebetween promotes the circulation of the liquid through the reactor.

The control of the reaction is preferably based on the temperature, as hereinbefore stated, though it may alternatively be based on the pH, or redox potential, as has hitherto been the case. More specifically, the supply of the feedstock to the reactor defining the second reaction zone is preferably so performed that the supply of chlorine is made through a port below that through which the reaction product of the first reaction zone is introduced, and is so controlled as to ensure that the mixture in the first reaction zone remain at a temperature of 5° C. to 20° C., while the reaction product of the first reaction zone is supplied at a constant rate by gravity, or through a pump.

A pipe connected to the top of the vertical loop-shaped reactor for defining a port through which unreacted chlorine gas is drawn out, preferably has an inside diameter equal to that of the uptake and downtake if the latter is smaller than 450 mm, or an inside diameter which is equal to at least three-fifths of that of the uptake and downtake if the latter is 450 mm or larger, so that the unreacted chlorine gas may be drawn out effectively without hindering the circulation of the reaction product through the reactor. The uptake and downtake preferably have a height which is at least 10 times larger than their diameter.

The slurry of trichloroisocyanuric acid which has been produced is discharged from the reactor at its bottom, is conducted through a rising pipe so as to maintain its surface level at a height above the top of the reactor, and is conveyed to a filtration zone.

It is known that the rate of the reaction for the production of trichloroisocyanuric acid depends on the dissolution of chlorine gas, as has already been stated. Moreover, it is necessary to chlorinate the reaction product from the first reaction zone quickly in order to minimize the formation of nitrogen trichloride and produce a stable slurry of trichloroisocyanuric acid. The effective dissolution of chlorine gas and the prevention of formation of nitrogen trichloride depend on the size of the area which is available in the second reaction zone for the dissolution of chlorine gas. Only a small area is, however, available in any reactor of the tank type and results, therefore, in a lower yield of chlorination. In order to create a larger area for the dissolution of chlorine gas in a reactor of the tank type, it is necessary to provide it with an undesirably large stirrer, a baffle, etc. to promote the circulation of the reactant solution and the dispersion and dissolution of chlorine gas therein.

The vertical loop-shaped reactor, on the other hand, enables the solution to circulate therethrough as effectively as a solution caused by a gas pump to flow through a pipe, and does not, therefore, create any dead space therein. It enables the circulation of a large amount of solution for its capacity and provides a large area for the dissolution of chlorine gas, thereby allowing for a high yield of reaction per unit volume of chlorine gas. Therefore, the vertical loop-shaped reactor does not call for any large stirrer as is required for a reactor of the tank type. The reactor permits only a smaller amount of nitrogen trichloride to be formed, and as the amount of the slurry which dwells in the reactor is smaller than in a reactor of the tank type, the loop-shaped reactor contains a smaller amount of nitrogen trichloride at any moment. This ensures a drastic reduction in the possibility of any abnormal reaction being caused by nitrogen trichloride. Moreover, the loop-ahaped reactor is smaller in diameter than any reactor of the tank type, and can accordingly be constructed with a smaller wall thickness. Therefore, and also as it requires no stirrer, the loop-shaped reactor is by far less expensive than any reactor of the tank type.

Still another advantage of the vertical loop-shaped reactor is due to the fact that it is substantially nothing but a simple pipeline and does not contain any auxiliary device such as a stirrer, or baffle, as opposed to any reactor of the tank type. It does not necessitate any cleaning that would otherwise be required for removing any crystal adhering to any such device and, therefore, make it necessary to stop the operation of the reactor frequently but can be used for a long period of continuous operation.

It has usually been the case that a temperature up to only 20° C. is allowable for the dissolution of chlorine as nitrogen trichloride has been more likely to form at a higher temperature. If a vertical loop-shaped reactor is used for the second reaction zone, however, a temperature up to as high as 35° C. is allowable, since the reactor provides a large area for the dissolution of chlorine and enables a reduction in the amount of nitrogen trichloride which is formed.

Attention is now directed to FIG. 1 showing by way of example a system which can be employed for carrying out a preferred mode of the process of this invention. An alkali salt of cyanuric acid which has been cooled to a temperature between above its solidifying point and 10° C. is continuously supplied to a reactor 4 defining a first reaction zone (hereinafter referred to as the first reactor) through a line 1, a pump 2 and a solenoid valve 3 by which its flow rate can be remotely controlled. A line 6 is connected to maintain a slightly negative pressure, or a pressure slightly lower than atmospheric pressure in the reactor 4. A pump 5 is provided for circulating a part of solution in the reactor 4. The alkali salt of cyanuric acid in the reactor 4 is partially chlorinated upon contacting unreacted chlorine arriving through a line 13, and is conveyed by gravity into a vertical loop-shaped reactor 12 defining a second reaction zone (hereinafter referred to as the second reactor) through a line 11.

Chlorine is supplied into the second reactor 12 through a line 9 connected to one of the two upstanding straight portions thereof near its lower end. The supply of chlorine is so controlled by a valve 10 which is remotely controlled by a valve controller 8, that a temperature measuring instrument 7 instrlled in the first reactor 4 and connected to the valve controller 8 may always indicate a temperature within the range of 5° C. to 20° C. The flow of chlorine gas into the reactor 12 is so directed that a slurry containing crystals of trichloroisocyanuric acid which is formed therein may be circulated clockwise as viewed in FIG. 1. The slurry is continuously discharged from the second reactor 12 into a line 14 connected to its bottom and leading to a filtration zone, so that the slurry in the second reactor 12 may always keep its surface level at a height above the top of the loop defining the reactor 12.

The invention will now be described more specifically with reference to a fes examples thereof.

EXAMPLE 1

The reaction system as shown in FIG. 1 was used. A gas absorption column having a diameter of 500 mm and a height of 2500 mm was used as the first reactor 4. It was so constructed as to hold 0.1 $m^3$ of reactant solution and enable its partial circulation through an external line. The second reactor 12 was a vertical loop-shaped reactor having a pipe diameter of 300 mm and a capacity of 1.8 $m^3$, while both of its uptake and downtake portions had a height of 10 m.

An alkali salt of cyanuric acid prepared by mixing cyanuric acid and sodium hydroxide in a molar ratio of 1:3 and having a cyanuric acid content of 50 g per liter was cooled to 2° C. by an effective cooler, and was supplied to the first reactor 4 at a flow rate of 6 $m^3$ per hour as controlled by the solenoid valve. Chlorine gas was supplied to the second reactor 12 at such a flow rate as to ensure that the reactant mixture in the first reactor 4 be maintained at a temperature of 10° C. plus or minus 1° C.

The slurry which had been produced in the second reactor 12 was continuously discharged from it at such a rate as to ensure that the slurry in the reactor 12 maintain its surface level at a height of about 500 mm above the top of the loop, and was conducted to filtration zone. The slurry in the second reactor 12 has a temperature of 24° C. to 28° C.

About two months of continuous operation yielded dry trichloroisocyanuric acid having a purity of 99.3% at an average rate of 360 kg per hour. In other words, as much as 200 kg of trichloroisocyanuric acid per hour was produced per $m^3$ of capacity of the reactor 12.

The production which has been achieved by the two months of continuous operation meant an average yield of 92% based on cyanuric acid, and 89% based on chlorine. It was not necessary at all to stop the operation during the two months' period to clean the reactors of any crystal adhering thereto. The rate of circulation of the slurry through the second reactor 12 was from 0.7 to 1.0 m per second throughout the period.

EXAMPLE 2

Figure 2:
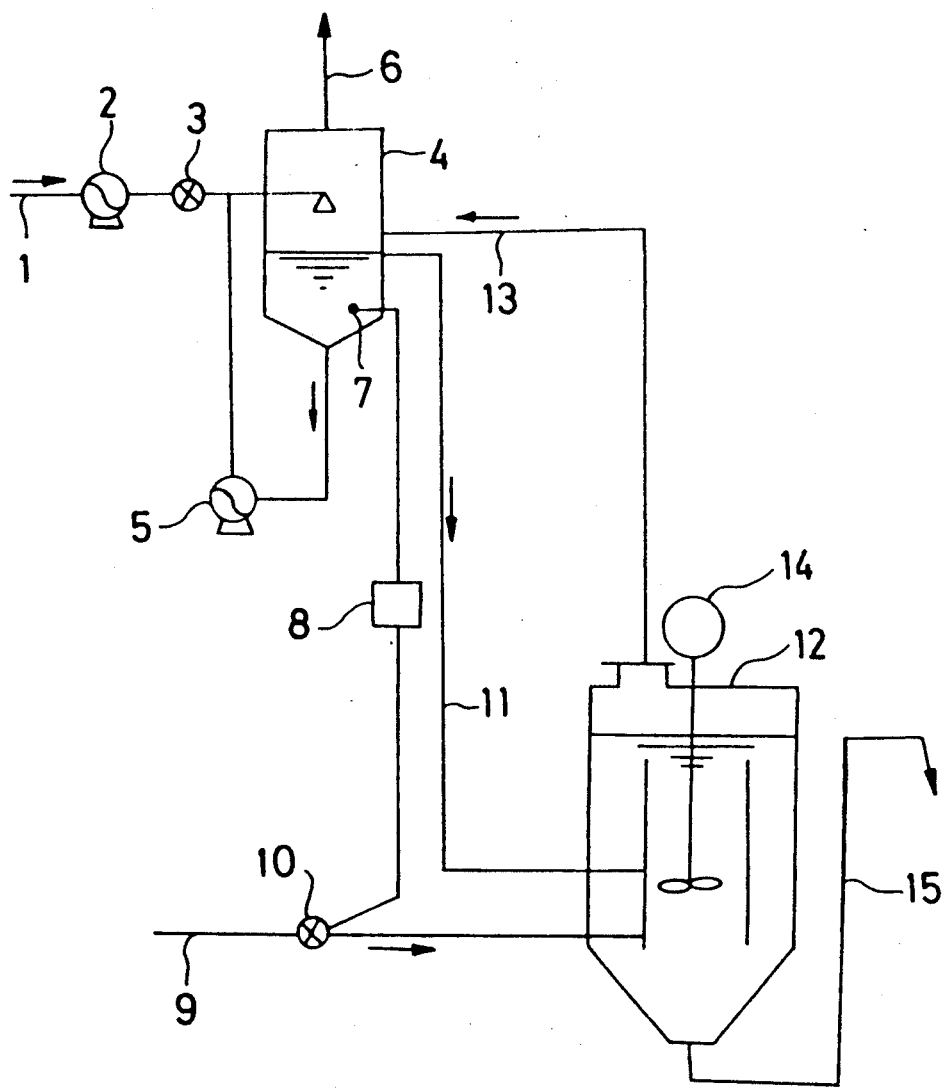
FIG. 2 is a block diagram of another reaction system including a second reaction zone defined by a reactor of the tank type.

A reaction system as shown in FIG. 2 was used. A gas absorption column having a diameter of 150 mm and a height of 750 mm was used as the first reactor 4. It was so constructed as to hold three liters of reactant mixture and enable its partial circulation through an external line. The second reactor 12 was a reactor of the tank type having a diameter of 440 mm, a height of 870 mm and a capacity of 130 liters, and provided with a stirrer and an inner cylinder.

An alkali salt of cyanuric acid prepared by mixing cyanuric acid and sodium hydroxide in a molar ratio of 1:3, and having a cyanuric acid content of 50 g per liter was cooled to 2° C. by an effective cooler, and was supplied to the first reactor 4 at a rate of 88 liters per hour as controlled by a solenoid valve 3. Chlorine gas was supplied to the second reactor 12 at such a rate as to ensure that the reactant mixture in the first reactor 4 be maintained at a temperature of 8° C. to 12° C The slurry which had been produced in the second reactor 12 was continuously discharged from it at such a rate as to ensure that the slurry in the reactor 12 maintain its surface level at a height of about 250 mm below the top of the reactor 12. The slurry was subjected to filtration to form a cake and the cake was dried in a drier.

The reaction system was operated for seven days on an eight hour per diem basis. The average results of the operation are listed below:

Dry cake obtained: 7.5 kg per hour
  Effective chlorine content: 90.1% on the average (89.5 to 90.7%)
  Purity: 98.4% on the average (97.7 to 99.0%)
  Yield: 89.9% based on cyanuric acid; 87.0% based on chlorine.

For the sake of comparison, a redox electrode was attached to a slurry discharge line 15 and the redox potential of a sample of slurry was measured by a portable redox potential measuring instrument. During the first three days, all the mersurements showed a normal value of redox potential within the range of 1110 mV plus or minus 10 mV. On the fourth day, however, the electrode started to indicated a value which was higher than that as measured by the portable instrument, and it showed a gradual increase thereafter until a maximum difference of 60 mV was observed. This was obviously due to the adherence of crystals to the electrode, as it restored its normal indication upon removal of crystals therefrom. These results confirm that the conventional process relying upon the redox potential of a slurry as measured by an electrode contacting it for the control of chlorine supply is difficult to employ for the stable production of trichloroisocyanuric acid over a long period of time.

What is claimed is:

1. In a process for producing trichloroisocyanuric acid which comprises supplying unreacted chlorine from a second reaction zone to a cooled mixture of cyanuric acid and an aqueous alkali solution in a first reaction zone to form a partially chlorination alkali salt of cyanuric acid, and introducing the reaction product of said first reaction zone and chlorine into said second reaction zone to complete the chlorination of said product, the improvement wherein the supply of said chlorine into said second reaction zone is so controlled as to ensure that said mixture in said first reaction zone be maintained at a temperature of 5° C. to 20° C.

2. A process as set forth in claim 1, wherein said temperature is between 8° C. and 15° C.

3. A process as set forth in claim 1, wherein said second reaction zone is defined by a vertically disposed loop-shaped reactor comprising two substantially straight upstanding tubular portions connected together at the upper and lower ends thereof to form a loop and defining an uptake and a downtake, respectively.

4. A process as set forth in claim 3, wherein said reaction product of said first reaction zone and said chlorine are introduced into said reactor near the lower end of said uptake, while said unreacted chlorine is drawn out of said reactor at its top for delivery into said first reaction zone, and a slurry of trichloroisocyanuric acid obtained as a result of said chlorination is discharged from said reactor at its bottom after circulation through said downtake.

* * * * *